United States Patent [19]

Samuelsen

[11] Patent Number: 4,604,095
[45] Date of Patent: Aug. 5, 1986

[54] RETURN VALVE FOR A BAG FOR COLLECTING LIQUID EXCRETIONS FROM THE HUMAN BODY

[75] Inventor: Peter Samuelsen, Rungsted Kyst, Denmark

[73] Assignee: Coloplast A/S, Denmark

[21] Appl. No.: 567,059

[22] Filed: Dec. 30, 1983

[30] Foreign Application Priority Data

Jan. 4, 1983 [DK] Denmark .................................. 10/83

[51] Int. Cl.$^4$ ............................................... A61M 1/00
[52] U.S. Cl. ...................... 604/323; 604/335; 604/350
[58] Field of Search .................. 137/846, 512, 512.1; 604/332-345, 323, 350; 383/44, 46, 48, 49, 51, 58, 61

[56] References Cited

U.S. PATENT DOCUMENTS

| 2,796,864 | 6/1957 | Johnson . | |
|---|---|---|---|
| 3,430,842 | 3/1969 | Yamaguchi | 383/44 |
| 3,822,720 | 7/1974 | Souza | 137/846 |
| 3,901,265 | 8/1975 | Groombridge | 137/512 |
| 4,084,590 | 4/1978 | Caraway | 604/335 |
| 4,533,354 | 8/1985 | Jensen | 604/323 |

FOREIGN PATENT DOCUMENTS 2249132 4/1973 Fed. Rep. of Germany .
2058011 4/1981 United Kingdom .

*Primary Examiner*—C. Fred Rosenbaum
*Assistant Examiner*—J. L. Kruter
*Attorney, Agent, or Firm*—Hall, Myers & Rose

[57] ABSTRACT

Return valve for a bag (1) for collecting liquid excretions from a human body, which valve comprises a valve flap (9,10) made of flexible film and placed between a reservoir portion (8) of the bag and a portion having a coupling to be connected with corresponding fastening means placed around an opening in the body. In order to ensure an extreme security against leakage through the return valve, the return valve further comprises a second valve flap (13, 14) arranged downstream of the first valve in the direction of the flow of the liquid secretions, which second valve flap comprises a film portion passing the opening (at 11) of the first valve, and together with the valve flap of the first valve forming a passage to the region between the first and second valves.

4 Claims, 4 Drawing Figures

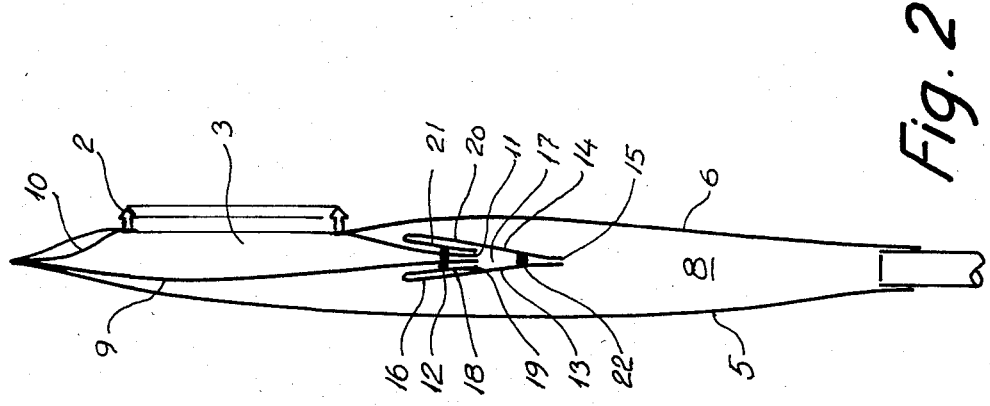
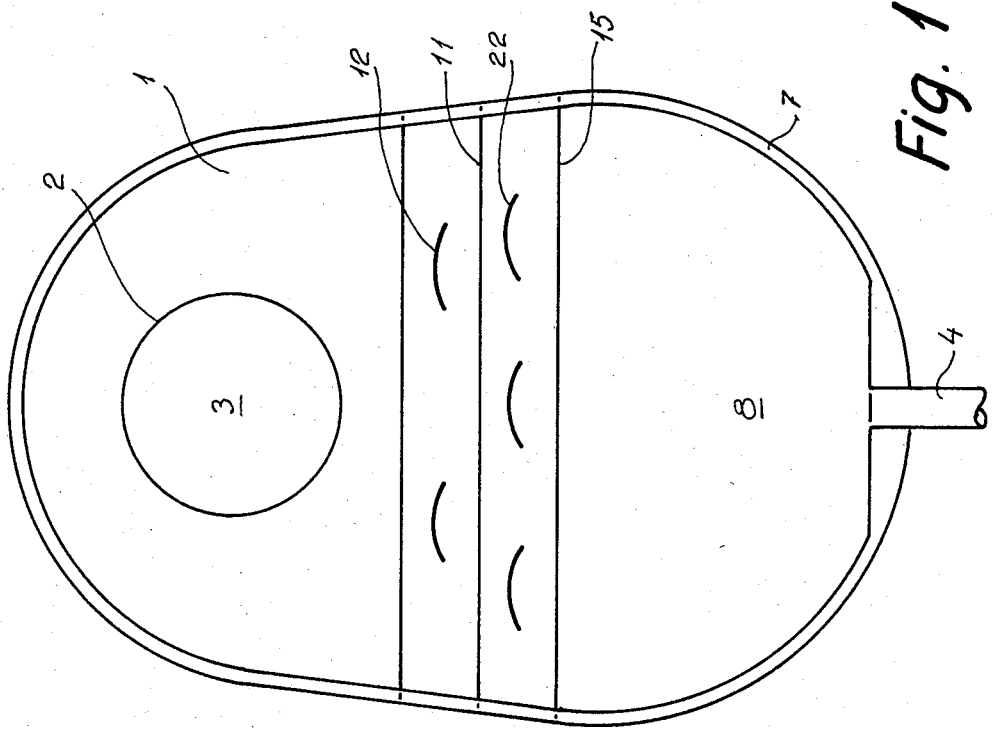

RETURN VALVE FOR A BAG FOR COLLECTING LIQUID EXCRETIONS FROM THE HUMAN BODY

FIELD OF THE INVENTION

The present invention relates to a return valve for a bag for collecting liquid excretions from the human body, said return valve being of the type comprising a valve flap made of a flexible film and placed between a reservoir portion of the bag and a portion having coupling means to be connected with corresponding fastening means placed around an opening in the body.

BACKGROUND ART

Valves of this type are preferably used by patients which have undergone stoma surgery. The excretion from the stoma should be allowed free passage to the reservoir of the bag, but must be prevented from passing backwards into the opening in the body of the patient, where it may cause an infection due to bacterial contamination of the contents of the bag, a deterioration of the general health of the patient resulting. As mentioned above known bags comprise a return valve in the shape of a flap of film resting against a film wall and with an opening facing downwards or two flags of film placed one on the other, said flaps also being provided with an opening face downwrads. Under normal conditions the foil flaps are able to ensure a total closure and besides they are simple and economical to produce, which makes it possible to discard the bag after a relatively short period of use in order to reduce the risk of contamination. However, the bag, which is being carried under the clothing of the patient, may under certain circumstances be bent or folded in such a way that the full flap is lifted from its abutment and the reservoir portion may incidentally be squeezed, its contents being pressed as a cascade against the return valve, which under such conditions has proved not to be as leakfree as under laboratory conditions.

SUMMARY OF THE INVENTION

Is is an object of the invention to improve the return valve in order to substantially reduce the risk of infection, the valve still being simple and economical to produce and still providing a free passage for the excretions.

The return valve according to the invention is characterized by the return valve further comprising a second valve flap arranged downstream to the first valve in the direction of flow of the liquid excretions, which second valve flap comprises a film portion passing the opening of the first valve and together with the first valve forming a passage to the reservoir portion of the bag.

The solution proposed in accordance with the invention comprises in reality two sets of valve flaps in series, but the downstream one is provided with a bypass allowing a possible wave of liquid to enter into the chamber between the two valves. As the downstream valve is a return valve, the major portion of the liquid leaking into the intermediate chamber will enter through the bypass passage, which is placed along the upstream valve and in its open direction. The upstream valve therefore gets very favourable working conditions, when the demands for tightness are strongest. Practical tests have proved the truth of the theory, and the arrangement ensures greater tightness than a bag with a single valve flap or with two valve flaps in series.

One embodiment of the return valve according to the invention and in accordance with claim 2 ensures an improved passage through the bypass passage, the working conditions of the upstream valve being further improved.

According to a preferred embodiment of the invention, in which the upstream valve flap consists of two abutting foils, the downstream valve flaps are arranged in abutment with both flaps of the upstream valve. Thereby, a symmetrical arrangement, in which nearly all pressures from the liquid on the valve flaps will be balanced, is obtained.

The invention will be further described in the following detailed description with reference to the drawings showing an embodiment of a collection bag for liquid excretions from the human body and comprising the return valve according to the invention.

BRIEF DESCRIPTION OF THE DRAWINGS

In the drawings

FIG. 1 shows the collecting bag in plane view,

FIG. 2 shows schematically a longitudinal section through the bag according to FIG. 1.

DESCRIPTION OF PREFERRED EMBODIMENTS

Figure 4:
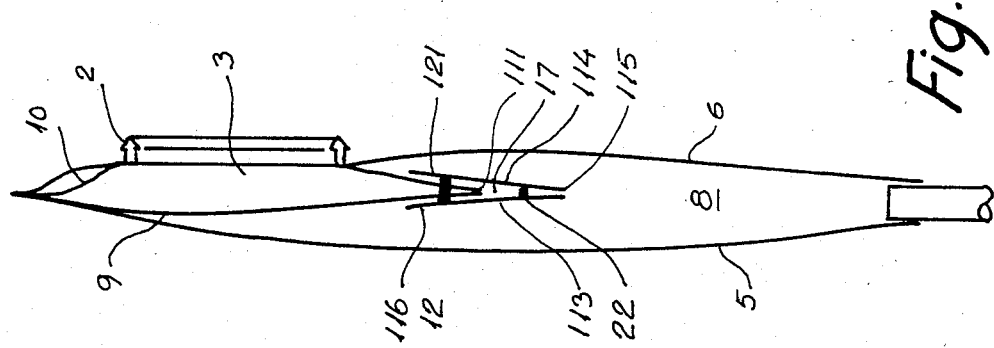
FIG. 4 shows schematically the bag according to FIG. 3 in longitudinal section view.

The return valve according to the invention is arranged in a bag 1 as shown in FIG. 1, the bag having coupling means 2 for fastening with an opening 3 placed inside the coupling means on line with a stoma, a fistula or a similar opening in a human body. The coupling means enables the bag 1 to be mounted on or removed from a plaster placed around the opening in the body and provided with corresponding coupling means. The bag may be attached direct to the body around the opening, in which case the coupling means is a ring of adhesive intended for attachment to the skin. The bag 1 may also be provided with a drain 4 at the lower and preferably wider portion, and the drain may be provided with a (not shown) closing valve.

As seen in FIG. 2 the bag comprises two plastic films 5,6, one forming the front 5 and the other one forming the back 6. The films are united along the edges by means of a welding 7 (FIG. 1). The space between the two films forms the reservoir portion 8 of the bag. The reservoir portion 8 is separated from the opening 3 by means of a return valve. This valve also comprises two films, the front film flap 9 and the rear film flap 10. The rear film flap is welded to the back 6 at the coupling means 2, and the two film flaps are welded together with the front and back film in the welding along the edge. The two film flaps pass the opening, but is cut off in some distance below the opening with the edges 11 at the same level. A short distance above the edges the two film flaps are welded together in small areas, for example along the lines 12. Excretions from the opening 3 may pass freely through the space between the film flaps 9 and 10 into the reservoir portion 8 of the bag 1. If the bag 1 is being hit or squeezed, the film flaps will be pressed against each other, thereby preventing the liquid from returning into the opening in the body.

However, such a simple valve is not sufficiently tight under all circumstances. If the bag is subject to pushing or squeezing and simultaneous bending, a pressure wave in the liquid may result in a leakage through the return valve. Therefore, around the return valve a secondary return valve is arranged. This secondary valve comprises two valve flaps 13,14, the lower edges 15 of which form a secondary return valve placed in series with the first one. Liquid introduced into the bag may freely pass the two return valves into the reservoir portion 8 of the bag. The valve flaps 13, 14 have, however, a film portion passing the lower edge 11 of the upper return valve. This film portion is welded together with the flaps of the upper valve along the lines 12. As the weldings are not continuous a bypass passage is formed between the film portion 16 and the valve flap 9 through which passage liquid from the reservoir portion may inter into the chamber 17 between the two valves and defined by the flaps 13,14. Liquid entering into the chamber is, however, moving in a direction opposite to a possible leakage through the upper return valve and will promote a pressing together of the two film flaps 9,10, thereby improving the functioning of the upper return valve. In order to reduce the possibility of the film portion 16 itself functioning as a return valve, the film portion 16 may have a folding 18 facing inwards against the valve flap 9, and the edge of the folding may be in line with the edge 11 of the valve flap 9. Correspondingly the other valve flap 14 may comprise a film portion 20 with a folding 21. The valve flaps 13,14 are welded together with the outer films along the edge and further welded together at lines 22.

Figure 3:
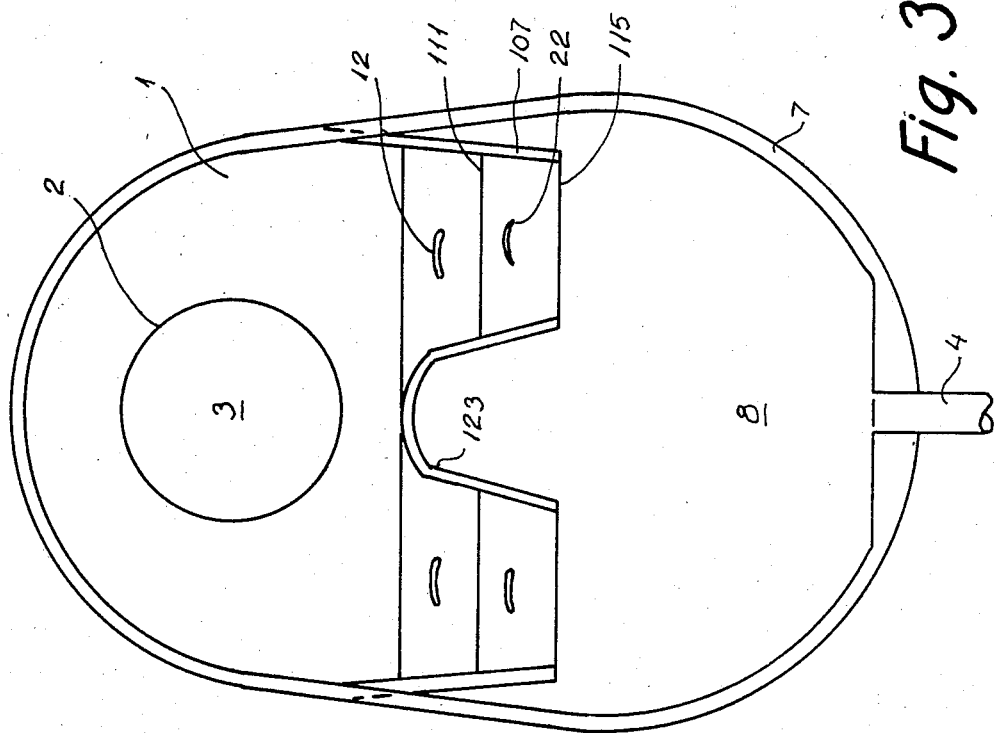
FIG. 3 shows a collecting bag in plane view with a modified return valve.

In FIGS. 3 and 4 a modified return valve is shown. The bag corresponds in its outer shape and coupling means to the bag according to FIG. 1, and corresponding parts bear the same reference numbers as in FIGS. 1 and 2. According to the modification the film flaps 9,10 are not welded into the joint between the front 5 and the back foil 6 from the level of the coupling means 2, but the two flaps are just welded together along the side edges 107 below this level. In order to reduce the length of the lower edge 111 of the flaps 9,10, a cut 123 has been made at the centre of the flaps, and the flaps have been welded together along this cut. The flaps are provided with a secondary return valve arrangement as described above. As seen from FIG. 4, the film portion 116 is not folded as shown in FIG. 2, but between the flaps 9 and 10 and the film portions 116 and 120, respectively, a passage is defined as described above.

Within the scope of the invention it is possible to simplify the return valve for example by arranging the return valves as a single flap being pressed against a continuous film wall. As an example of such a simplification, the valve flap 10 may be extended to the level of the edge 15 or both the valve flap 10 and 14 can be omitted, the back film 6 being used as a continuous film wall. In this case the valve flaps 9 and 13 are welded to the film 6 at weldings 12 and 22.

I claim:

1. In a bag for collecting liquid excretions from a body comprising coupling means for attachment to fastening means placed around an opening in the body, a drainage inlet for a liquid collection reservoir, a first return valve means of plural films having an inner and outer face, said valve means being located between the drainage inlet and the reservoir in the shape of at least one film flap resting against a film wall and having a downward-facing opening, and reservoir means for collecting said liquid excretions, the improvement which comprises:
    (a) means for diverting the flow of said liquid excretions between the drainage inlet and the reservoir means;
    (b) a second return valve means of plural films having an inner and outer face located downstream from and in series with the direction of flow of the first return valve means, the second return valve means being in the shape of at least one film flap resting against a film wall and having a downward-facing opening into said reservoir means;
    (c) an intermediate fluid-collecting chamber between the first and second return valve means; and
    (d) by-pass passage means, formed by discontinuous horizontally extending bonds between an outer face of the upstream first return valve means and the inner face of the second valve means and in its open position for receiving liquid from the reservoir and directing it into the intermediate chamber between the first and second return valve means whereby to return the liquid to the reservoir means exteriorly of the outer faces of the first and second valve means and therefore avoid backup of body excretions.

2. An apparatus according to claim 1, wherein the film portion of the second return valve means is folded along an edge which is at the same level as the lower edge of the first return valve means.

3. An apparatus according to claim 1 wherein the means for diverting the flow of said liquid excretions between the drainage inlet and the reservoir means are film walls of the second return valve which is positioned between the drainage inlet and the reservoir means.

4. An apparatus according to claim 1 wherein the means for diverting the flow of said liquid excretions between the drainage inlet and the reservoir means is a sealed portion of the film wall of at least one of the first or the second return valve means which is positioned between the drainage inlet and the reservoir means.

* * * * *